US012260677B2

United States Patent
Chan et al.

(10) Patent No.: US 12,260,677 B2
(45) Date of Patent: Mar. 25, 2025

(54) PRIVACY-PRESERVING HUMAN ACTION RECOGNITION, STORAGE, AND RETRIEVAL VIA JOINT EDGE AND CLOUD COMPUTING

(71) Applicant: AltumView Systems Inc., Burnaby (CA)

(72) Inventors: Chi Chung Chan, Burnaby (CA); Dong Zhang, Port Coquitlam (CA); Yu Gao, North Vancouver (CA); Andrew Tsun-Hong Au, Coquitlam (CA); Zachary DeVries, Langley (CA); Jie Liang, Coquitlam (CA)

(73) Assignee: Altum View Systems Inc., Burnaby (CA)

( * ) Notice: Subject to any disclaimer, the term of this patent is extended or adjusted under 35 U.S.C. 154(b) by 496 days.

(21) Appl. No.: 17/522,901

(22) Filed: Nov. 9, 2021

(65) Prior Publication Data

US 2022/0147736 A1 May 12, 2022

Related U.S. Application Data

(60) Provisional application No. 63/111,621, filed on Nov. 9, 2020.

(51) Int. Cl.
*G06K 9/00* (2022.01)
*G06F 21/62* (2013.01)
(Continued)

(52) U.S. Cl.
CPC .......... *G06V 40/23* (2022.01); *G06F 21/6245* (2013.01); *G06T 13/40* (2013.01); *G06V 20/41* (2022.01); *G06V 40/166* (2022.01)

(58) Field of Classification Search
CPC ...... G06V 40/23; G06V 20/41; G06V 40/166; G06V 10/82; G06V 20/52; G06V 40/161;
(Continued)

(56) References Cited

U.S. PATENT DOCUMENTS 7,541,934 B2 * 6/2009 Fredriksson ....... G08B 21/0476
340/573.7
7,746,345 B2 * 6/2010 Hunter .................... G06T 13/40
345/475

(Continued)

OTHER PUBLICATIONS

Ghidoni, Stefano, et al. "A multi-viewpoint feature-based re-identification system driven by skeleton keypoints." Robotics and Autonomous Systems 90 (2017), pp. 45-54 (Year: 2017).*

(Continued)

*Primary Examiner* — Alex Kok S Liew

(57) ABSTRACT

The present disclosure provides a method and system for efficiently and securely managing human motion data. In one aspect, a human-motion-data-managing system first receives a sequence of video images including a first person. Next, for each image in the sequence of video images, the human-motion-data-managing system detects the first person in the video image; and subsequently extracts a skeleton figure of the detected first person from the image, wherein the skeleton figure is composed of a set of human keypoints. Next, human-motion-data-managing system combines a sequence of extracted skeleton figures of the detected first person from the sequence of video images to form a skeleton sequence of the detected first person which depicts a continuous motion of the first person. The human-motion-data-managing system subsequently transmits the skeleton sequence to a server in place of the actual images of the first person to preserve the privacy of the first person.

20 Claims, 7 Drawing Sheets

(51) Int. Cl.
*G06T 13/40* (2011.01)
*G06V 20/40* (2022.01)
*G06V 40/16* (2022.01)
*G06V 40/20* (2022.01)

(58) Field of Classification Search
CPC .. G06V 40/20; G06V 20/46; G06V 2201/033; G06F 21/6245; G06F 21/6254; G06T 13/40; G06T 2210/08; G06T 2210/41; G06T 17/00; G16H 30/40; G16H 50/20
See application file for complete search history.

(56) References Cited

U.S. PATENT DOCUMENTS

| | | | | |
|---|---|---|---|---|
| 2010/0328436 | A1* | 12/2010 | Skubic | A61B 5/0022 348/47 |
| 2012/0209149 | A1* | 8/2012 | Yoneyama | A61B 5/7246 600/595 |
| 2013/0097508 | A1* | 4/2013 | Matejka | H04N 21/6587 715/720 |
| 2015/0213702 | A1* | 7/2015 | Kimmel | G06V 20/52 382/103 |
| 2015/0269744 | A1* | 9/2015 | Mukherjee | G06V 40/23 382/103 |
| 2019/0138748 | A1* | 5/2019 | Long | H04N 7/183 |
| 2019/0205630 | A1* | 7/2019 | Kusens | A61B 5/6891 |
| 2019/0259136 | A1* | 8/2019 | Shpalensky | G06T 7/70 |
| 2019/0349554 | A1* | 11/2019 | Derenne | A61B 5/1113 |
| 2020/0211154 | A1* | 7/2020 | Ng | G16H 30/40 |
| 2020/0288308 | A1* | 9/2020 | Jimenez | H04W 12/033 |
| 2020/0349347 | A1* | 11/2020 | Morzhakov | G06V 20/52 |
| 2022/0072377 | A1* | 3/2022 | Russell | G06V 10/25 |

OTHER PUBLICATIONS

Lee, Bokyung, et al. "Semantic human activity annotation tool using skeletonized surveillance videos." Proceedings of the 2019 ACM International Symposium on Wearable Computers. 2019, pp. 312-315 (Year: 2019).*

Chen, Weiming, et al. "Fall detection based on key points of human-skeleton using openpose." Symmetry 12.5 (May 5, 2020), pp. 1-17 (Year: 2020).*

* cited by examiner

PRIVACY-PRESERVING HUMAN ACTION RECOGNITION, STORAGE, AND RETRIEVAL VIA JOINT EDGE AND CLOUD COMPUTING

PRIORITY CLAIM AND RELATED PATENT APPLICATIONS

This application claims the benefit of priority under 35 U.S.C. 119(e) to U.S. Provisional Patent Application No. 63/111,621, entitled "Skeleton-Based Low-Cost Structured Human Action Data Recording, Storage, Retrieval, and Inference," by inventors Jie Liang, Andrew Tsun-Hong Au, Chi Chung Chan, Dong Zhang, and Eric Honsch, filed on 9 Nov. 2020, the contents of which are incorporated by reference herein.

TECHNICAL FIELD

The disclosed embodiments generally relate to the field of human activity, health, and wellness monitoring. More specifically, the disclosed embodiments relate to devices, systems and techniques for performing privacy-preserving human-activity data collection, recognition, transmission, storage and retrieval by combining local pre-processing at the data source and remote post-processing at a cloud server.

BACKGROUND

Video-based human action recognition refers to the technology of automatically analyzing human actions based on captured videos and video images of a single person or a group of people. For example, one particularly useful application of video-based human action recognition is for monitoring health and wellness of individuals based on video images captured by surveillance video cameras. However, one problem associated with traditional video surveillance technologies is that they cannot protect the privacy of the users, e.g., if the recorded surveillance videos stored in a local or remote server are accessed by hackers. As a result, traditional surveillance cameras are usually used to monitor outdoor/public areas, while being prohibited for use in private areas such as bedrooms and bathrooms. However, sometimes it may be necessary to monitor these private areas, e.g., to detect emergency events of seniors such as personal falls, especially those who live alone. It may also become necessary to use cameras in such private settings for doctors to remotely observe the activities of patients with certain diseases, such as dementia, Parkinson's, and depression.

Another problem associated with traditional video surveillance technologies is that processing and storing the recorded videos often require a huge amount of transmission bandwidth and storage space. Note that the flexibility and ability to analyze the recorded video content at a later time to detect and determine temporal and spatial events, persons and objects in the recorded videos are required by many applications. However, to allow future video content retrieval and analysis, the recorded videos often need to be first transmitted to a remote server and then stored in the cloud. Typically, a one-hour 360p recorded video will need 450 megabytes (MB) of storage space, a 24-hour 360p recorded video will need ~10.8 gigabytes (GB) of storage space, and one month of such low-resolution recorded videos will need 324 GB of storage space. If such videos are stored on the Amazon AWS cloud server, the unit cost would be $0.023/GB/month, so that the monthly cost for one-month 360p videos storage would be about $7.452. However, the storage cost will be much higher for higher resolution videos. As a result, existing home surveillance cameras cannot save too many videos in the cloud for too long. A typical approach is to store the motion-triggered video clips or continuous video records in the cloud temporarily for a few days up to one month, and a user needs to pay a monthly fee ranging from $1.49 to $30 per camera.

SUMMARY

Various embodiments of predicting human actions are disclosed. In one aspect, a human action prediction system first receives a sequence of video images including at least a first person. Next, for each image in the sequence of video image, the human action prediction system detects the first person in the video image; and subsequently extracts a skeleton figure of the detected first person from the detected image of the first person, wherein the skeleton figure is composed of a set of human keypoints of the detected first person. Next, human action prediction system combines a sequence of extracted skeleton figures of the detected first person from the sequence of video images to form a first skeleton sequence of the detected first person which depicts a continuous motion of the detected first person. The human action prediction system subsequently transmits the first skeleton sequence of the detected first person to a server, wherein transmitting the first skeleton sequence of the detected first person in place of the detected images of the first person to the server preserves the privacy of the detected first person.

BRIEF DESCRIPTION OF THE DRAWINGS

Features of the subject technology are set forth in the appended claims. However, for purpose of explanation, several embodiments of the subject technology are set forth in the following figures.

DETAILED DESCRIPTION

The following description is presented to enable any person skilled in the art to make and use the present embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present embodiments. Thus, the present embodiments are not limited to the embodiments shown, but are to be accorded the widest scope consistent with the principles and features disclosed herein.

The data structures and code described in this detailed description are typically stored on a computer-readable storage medium, which may be any device or medium that can store code and/or data for use by a computer system. The computer-readable storage medium includes, but is not limited to, volatile memory, non-volatile memory, magnetic and optical storage devices such as disk drives, magnetic tape, CDs (compact discs), DVDs (digital versatile discs or digital video discs), or other media capable of storing computer-readable media now known or later developed.

The methods and processes described in the detailed description section can be embodied as code and/or data, which can be stored in a computer-readable storage medium as described above. When a computer system reads and executes the code and/or data stored on the computer-readable storage medium, the computer system performs the methods and processes embodied as data structures and code and stored within the computer-readable storage medium. Furthermore, the methods and processes described below can be included in hardware modules. For example, the hardware modules can include, but are not limited to, application-specific integrated circuit (ASIC) chips, field-programmable gate arrays (FPGAs), and other programmable-logic devices now known or later developed. When the hardware modules are activated, the hardware modules perform the methods and processes included within the hardware modules.

Terminology

Throughout this patent disclosure, the terms "human action" and "human activity" are used interchangeably to mean a continuous motion of a person which can be captured by a sequence of video frames in a video. Moreover, the term a "video frame" refers to a single frame of video image/still image within a captured video.

Proposed Joint Human Action Recognition System Overview

Figure 1:
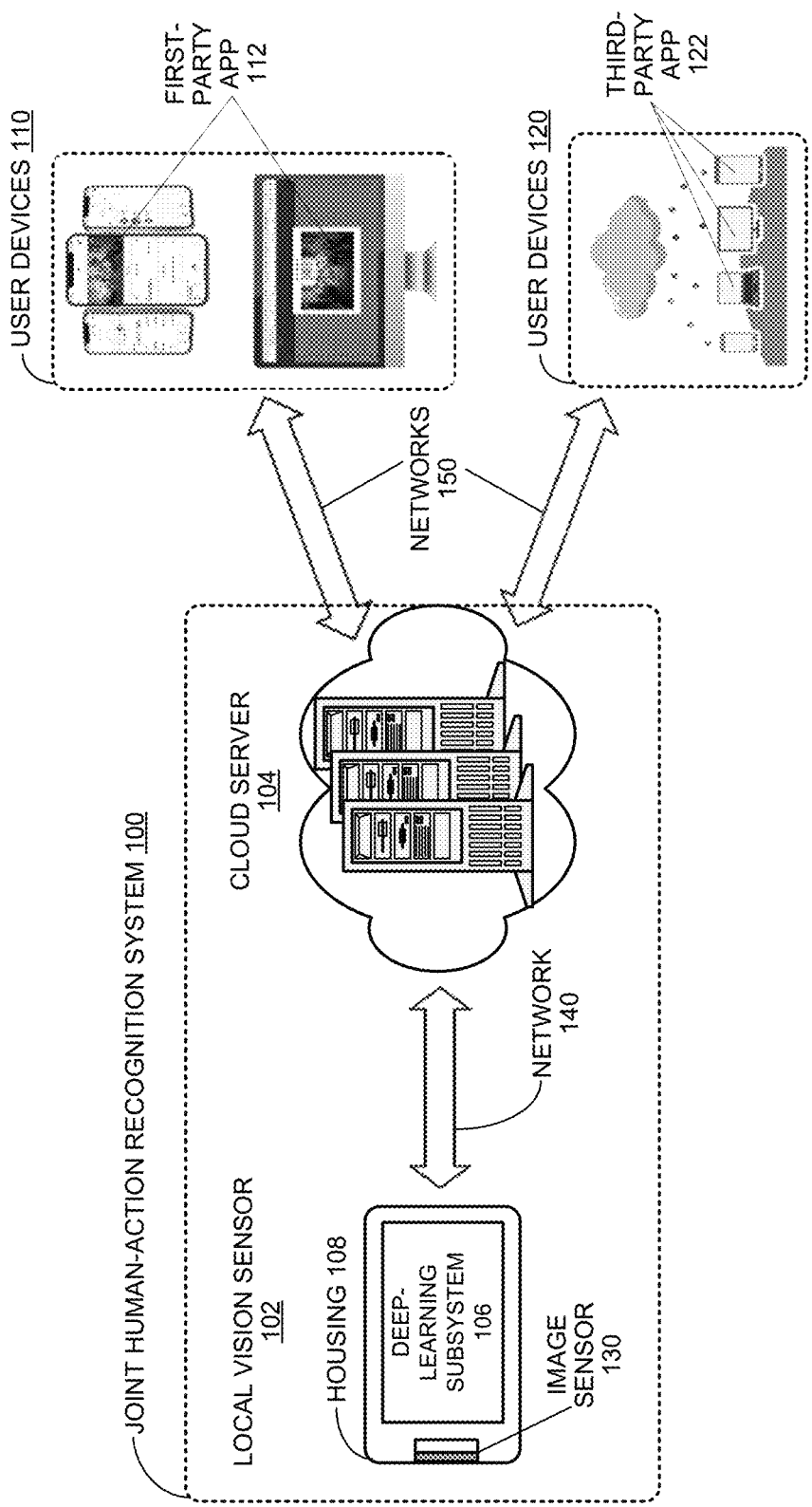
FIG. 1 illustrates a block diagram of a disclosed joint human-action recognition system including at least one local vision sensor and a cloud-based server in accordance with some embodiments described herein.

FIG. 1 illustrates a block diagram of a disclosed joint human-action recognition system 100 including at least one local vision sensor 102 and a cloud-based server 104 in accordance with some embodiments described herein. As can be seen in FIG. 1, joint human-action recognition system 100 includes at least one local vision sensor 102. However, the disclosed joint human-action recognition system can generally include any number of local vision sensors. Generally speaking, local vision sensor 102 is an intelligent vision system (which is sometimes referred to as an "intelligent camera" or "smart camera") that includes a built-in image sensor (e.g., a charge-coupled device (CCD) or a complementary metal-oxide-semiconductor (CMOS) camera), one or more processors for performing specific image processing on the images captured by the build-in image sensor, and a housing 108 that encapsulates the image sensor and the processors. Local vision sensor 102 can be installed or otherwise located at a place where certain human actions/activities of one or more persons need to be monitored. For example, local vision sensor 102 can be installed at an assisted living facility, a nursing care home, or a private home, and the one or more persons being monitored can be elderly people living in the assisted living facility, the nursing care home, or the private home.

In some embodiments, local vision sensor 102 can include a image sensor 130 (e.g., a CCD or a CMOS camera) for capturing raw videos of a space or an area that can include one or more persons being monitored, and a deep learning-based image-processing subsystem 106 (or "deep-learning subsystem 106") that includes both hardware processors and software modules for processing the captured videos and video frames. More specifically, the disclosed deep-learning subsystem 106 is configured to process captured video frames locally and in real-time to detect one or more monitored persons in the captured video frames, and to extract also in real-time, skeleton figures and as a result, skeleton sequences for the one or more detected persons from the captured video frames. In some embodiments, deep-learning subsystem 106 includes functionalities to remove, replace, or otherwise de-identify each detected person in a given video frame after extracting the corresponding skeleton figures/skeleton sequences of the detected person from the captured video frames. For example, deep-learning subsystem 106 can replace the processed video frames with the corresponding extracted skeleton sequences and a common background image to be stored locally. In some embodiments, the raw video frames that have been processed by deep-learning subsystem 106 can be permanently deleted.

In some embodiments, deep-learning subsystem 106 is configured to separately capture (e.g., before capturing the video frames) a background image of the monitored space/area without any person in the image. After a video of the monitored space/area is captured, deep-learning subsystem 106 is used to extract the skeleton sequences of one or more detected persons from the captured video frames. Next, the extracted skeleton sequences can be transmitted to cloud-based server 104 (or "cloud server 104" hereinafter) along with the background image. Because the transmitted skeleton sequences of the detected persons and the background image do not include any personal identifiable information (PII), the privacy of the detected persons is preserved and protected. Note that this background image associated with the captured video frames only needs to be transmitted to cloud server 104 once, until the background image is updated on local vision sensor 102. Hence, at a later time, the recorded scene/action sequences in the captured video frames can be reconstructed on cloud server 104 by overlaying the extracted one or more skeleton sequences onto the background image to form a new and sanitized video clip.

Note that local vision sensor 102 generally has limited computational resources, including limited computational power and storage space. In some embodiments, local vision sensor 102 can perform some simple action recognition functions using either the raw video frames or the extracted skeleton sequences. These simple action recognition functions can include, but are not limited to: recognition of standing, sitting down, lying down, fall, and waving hand. However, local vision sensor 102 is generally not designed to and hence not used to perform more complex action/activity recognitions, especially those actions that need long-time data, such as eating, cooking, quality of service of care workers, or diagnosis of certain behavioral diseases such as dementia, Parkinson's, and depression. By not performing the above complex action recognition functions, local vision sensor 102 can utilize its limited computational power and storage space to extract skeleton sequences for one or more detected persons in real-time, and transmit the extracted skeleton sequences in real-time to cloud server 104. As such, more complex action recognitions can be performed in real-time or offline on the cloud server based on the received skeleton sequences from local vision sensor 102. Local vision sensor 102 is described in more detail below in conjunction with FIG. 2.

Note that local vision sensor 102 is coupled to cloud server 104 through a network 140. Local vision sensor 102 configured to transmit real-time sanitized/de-identified human-action data including the skeleton sequences of the detected people to cloud server 104. Note that this real-time human-action data has a very small data size and hence requires very little network bandwidth for transmission. Cloud server 104 is configured to receive real-time sanitized/de-identified human-action data including the above-described skeleton sequences of the detected people from local vision sensor 102. Cloud server 104 is further configured to re-organize the received skeleton sequences, including indexing the received skeleton sequences based on one or more data attributes. These data attributes that can be used to index the received skeleton sequences can include, but are not limited to: people IDs, camera IDs, group IDs (e.g., people that belong to different monitoring groups), and recording timestamps. For example, cloud server 104 can be configured to re-organize the received skeleton sequences based on different people IDs that are used to differentiate skeleton sequences of different people. Cloud server 104 is further configured to store the indexed/structured skeleton sequences into an indexing database which can be efficiently searched, queried, and post-processed by an external user application (or "App") or by an internal data-processing module such as a complex action recognition module described below. Note that the received skeleton sequences can also be stored un-indexed or semi-indexed on a mass storage on cloud-based server 104. As described below, storing skeleton sequences in place of raw video images provides an extremely low-cost and privacy-preserving option for users who have need to store many hours of the recorded human action data temporarily or permanently.

Cloud server 104 is additionally configured to perform real-time or offline action recognition based on the received skeleton sequences. For real-time action recognition, cloud server 104 can directly receive real-time skeleton sequences from local vision sensor 102, process the received skeleton sequences to generate complex action/activity predictions using deep-learning techniques and big-data analytics. Because cloud server 104 includes significantly higher computational resources and storage space than local vision sensor 102, cloud server 104 is able to comfortably process the real-time skeleton sequences using high-complexity deep-learning algorithms and big-data analytics for any number of detected people and generate real-time human action/activity predictions based on the real-time skeleton sequences. Consequently, local vision sensor 102 and cloud server 104 operate collectively and concurrently to achieve privacy-preserving complex human action recognitions for multiple detected people in real-time. Alternatively, for offline action recognition, cloud server 104 can retrieve stored indexed skeleton sequences from an indexing database on cloud server 104, process the indexed skeleton sequences to generate human action predictions that require long-term data.

Referring back to FIG. 1, note that the disclosed joint human-action recognition system 100 can be coupled to various user devices through various networks 150. More specifically, the disclosed joint human-action recognition system 100 can be coupled to a first set of user devices 110 which run the first-party video-monitoring App 112 developed in conjunction with the disclosed joint human-action recognition system 100. Note that first-party video-monitoring App 112 can include a mobile version running on mobile devices and a web version running on desktop devices. Moreover, the disclosed joint human-action recognition system 100 can also be coupled to a second set of user devices 120 which run various third-party Apps 122 that can access the stored skeleton sequences on cloud server 104 of the disclosed joint human-action recognition system 100. Note that third-party video-monitoring Apps can also include third-party mobile Apps running on mobile devices and third party web-Apps running on desktop devices.

Figure 2:
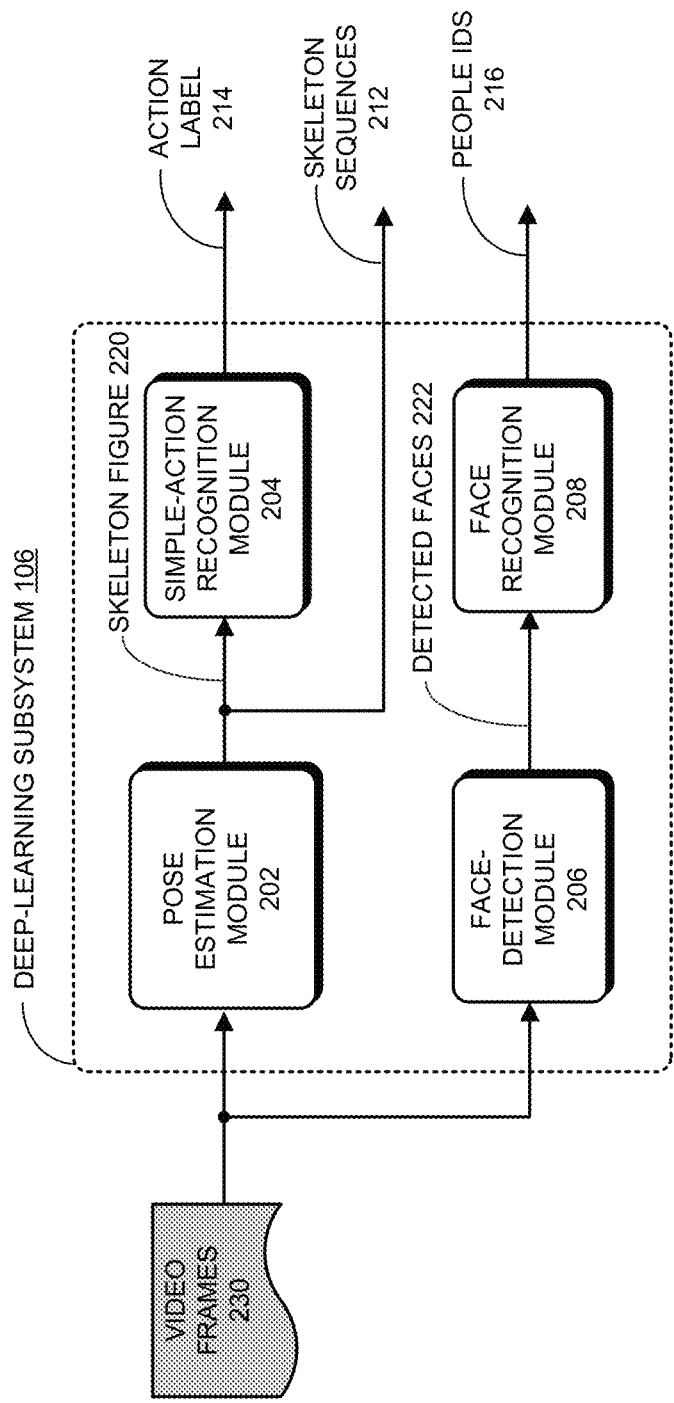
FIG. 2 shows a block diagram of the deep-learning subsystem of the disclosed local vision sensor within the disclosed joint human-action recognition system in accordance with some embodiments described herein.

FIG. 2 shows a block diagram of the deep-learning subsystem 106 of the disclosed local vision sensor 102 within the disclosed joint human-action recognition system 100 in accordance with some embodiments described herein. As can be seen in FIG. 2, deep-learning subsystem 106 can include: a pose-estimation module 202, a simple-action recognition module 204, a face-detection module 206, and a face-recognition module 208, each of the modules 202-208 performs specific deep-learning-based image processing computations. In some embodiments, deep-learning subsystem 106 can be implemented by one or more artificial intelligent (AI) processors. Note that other embodiments of deep-learning subsystem 106 of the disclosed local vision sensor 102 can include additional functional modules or omit one or more of the functional modules shown in FIG. 2 without departing from the scope of the present disclosure. For example, some embodiments of the disclosed local vision sensor 102 can also include a scene-segmentation/object-recognition module for detecting non-human objects in the recorded video frames.

In the embodiment shown, deep-learning subsystem 106 receives a sequence of video frames 230 as input. In some embodiments, the sequence of video frames 230 is a video segment of a predetermined duration within a recorded video. Note that video frames 230 are also referred as raw video images/frames because they are the output of image sensor 130 and have not yet been processed. Deep-learning subsystem 106 is configured to perform various deep-learning-based video image processing tasks on video frames 230 including, but are not limited to: (1) detecting each person and extracting skeleton figures and skeleton sequences from the sequence of video frames 230 using pose estimation module 202; (2) estimating some simple human actions for each extracted skeleton figure using simple-action recognition module 204; (3) detecting faces from video frames 230 using face-detection module 206; and (4) performing face recognitions on the detected faces using face-recognition module 208. In some embodiments, simple-action recognition module 204 also includes functionalities to identify certain emergency events, such as a fall, based on the estimated simple-human-actions, and subsequently generating emergency alarms/alerts.

In some embodiments, pose estimation module 202 is configured to process the sequence of video frames 230 to detect each and every person captured in each video image/frame of the sequence of video frames 230. Specifically, pose estimation module 202 is configured to detect each person within each image/frame of the sequence of video frame 230 and generate a set of keypoints of human body (also referred to as "human keypoints" or simply "keypoints" hereinafter) of the detected person. For example, a set of keypoints of the human body can include the eyes, the nose, the ears, the chest, the shoulders, the elbows, the wrists, the knees, the hip joints, and the ankles of the detected person. More specifically, each generated keypoint in the set of keypoints can be represented by: a keypoint index corresponding to a particular body joint (e.g., "0" for the nose; "1" for the chest, etc.); either a two-dimensional (2D) location (i.e., a set of X- and Y-coordinates in a 2D plane), or a three-dimensional (3D) location (i.e., a set of X-, Y-, and Z-coordinates in a 3D space); as well as a probability value for the predicted body joint associated with the generated keypoint.

Note that each set of keypoints extracted from a single video frame form a keypoint-skeleton representation of the detected person in the given video frame. In the discussion below, we refer to the set of human keypoints identified and extracted from a detected person image within a single video frame as the "skeleton figure" or the "skeleton representation" of the detected person in the given video frame. We further refer to a sequence of such skeleton figures extracted from a sequence of video frames as a "skeleton sequence" of the detected person. Hence, after processing the sequence of video frames 230, pose estimation module 202 outputs one or more skeleton sequences 212 of one or more detected persons in the sequence of video frames 230, wherein each skeleton sequence further comprises a sequence of individual skeleton figures of a particular detected person.

More detail of pose estimation module 202 is described in U.S. patent application Ser. No. 16/672,432, filed on 2 Nov. 2019 and entitled "METHOD AND SYSTEM FOR PRIVACY-PRESERVING FALL DETECTION," the content of which is incorporated herein by reference.

Figure 3:
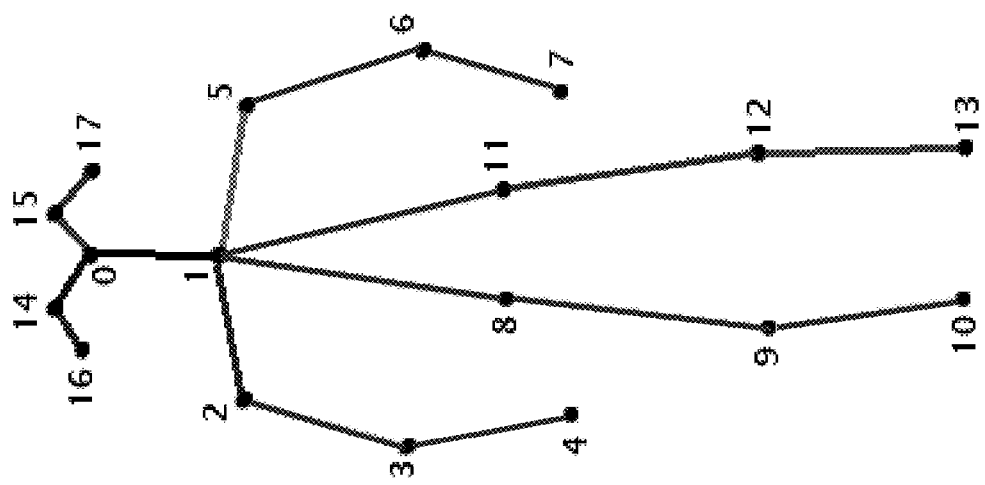
FIG. 3 shows an exemplary skeleton figure of a detected person generated by the pose estimation module using 18 keypoints to represent a human body in accordance with some embodiments described herein.

FIG. 3 shows an exemplary skeleton FIG. 300 of a detected person generated by pose estimation module 202 using 18 keypoints to represent a human body in accordance with some embodiments described herein. However, other embodiments of pose estimation module 202 can use fewer or greater than 18 keypoints to represent a human body. For example, instead of using the illustrated 18 keypoints, another embodiment of pose estimation module 202 can use just the head, the shoulders, the arms, and the legs of the detected person to represent a human body, which is a subset of the 18-keypoint representation. Yet another embodiment of pose estimation module 202 can use significantly more than the illustrated 18 keypoints of the detected person to represent a human body. Note that even when a predetermined number of keypoints is used by pose estimation module 202 for skeleton-figure extraction, the actual number of the detected keypoints of each extracted skeleton figure of each detected person can change from one video frame to the next video frame. This is because a part of a body of a detected person can be blocked by another object, another person, or by another part of the same body in some video frames, while no blocking of the body in some other video frames.

Moreover, a sequence of skeleton figures of a particular detected person extracted from the sequence of video frames 230 forms a "skeleton sequence" of the detected person, which represents a continuous motion of the detected person. Note that based on an extracted skeleton sequence of a detected person, the action of the detected person can be predicted. In the disclosed joint human-action recognition system 100, if this action recognition is determined to be too difficult for the local vision sensor 102 (e.g., measured by the inference speed and accuracy), this action recognition can be implemented and performed at cloud server 104. In this case, local vision sensor 102/deep-learning subsystem 106 simply outputs one or more extracted skeleton sequences 212 for one or more detected persons in video frames 230, wherein each extracted skeleton sequence 212 for each detected person further includes a sequence of extracted skeleton figures of the detected person. As described above, each extracted skeleton figure in skeleton sequences 212 is composed of a set of extracted keypoints. In some embodiments, each extracted keypoint in the set of extract keypoints is defined by: a keypoint index corresponding to a particular body joint; either a set of 2D X and Y-coordinates in a 2D plane, or a set of 3D X-, Y-, and Z-coordinates in a 3D space; and a probability value for the predicted body joint of that keypoint.

In some embodiments, one or more extracted skeleton sequences 212 of one or more detected persons from the sequence of video frames 230 can be buffered for a predetermined time interval (e.g., between 10 seconds to a few minutes) without immediate transmission to cloud server 104. Note that each buffered skeleton sequence can include one or more sequences of human actions performed by each detected person during the predetermined time interval. Next, at the end of the predetermined time interval, the entire buffered skeleton sequence(s) can be transmitted from local vision sensor 102 to cloud server 104 through a network 140. This buffered technique can reduce the access cost to the cloud server.

In some embodiments, simple-action recognition module 204 in deep-learning subsystem 106 is configured to receive an extracted skeleton FIG. 220 of a detected person in a given video frame 230, perform a deep-learning-based action recognition based on the configuration of skeleton FIG. 220 and/or localizations of the associated set of keypoints, and subsequently generate an action label 214. Note that this action label 214 represents a predicted pose or simple action for the detected person in the given video frame. As described above, the types of simple actions that can be predicated by simple-action recognition module 204 can include standing, sitting down, lying down, fall, and waving hand. In some embodiments, action label 214 can be combined with the corresponding extracted skeleton FIG. 220 as a part of the corresponding skeleton sequence 212 output. More detail of simple-action recognition module 204 is described in U.S. patent application Ser. No. 16/672,432, filed on 2 Nov. 2019 and entitled "METHOD AND SYSTEM FOR PRIVACY-PRESERVING FALL DETECTION," the content of which is incorporated herein by reference.

Referring back to FIG. 2, note that deep-learning subsystem 106 in local vision sensor 102 also includes face-detection module 206 configured to receive video frames 230 and output detected faces 222 corresponding to the detected persons by pose estimation module 202. Deep-learning subsystem 106 additionally includes face-recognition module 208 configured to perform face recognition functions based on the detected faces 222 from face-detection module 206, and subsequently generate people IDs 216 that correspond to and differentiate different detected persons by pose estimation module 202. In some embodiments, each person ID 216 within people IDs 216 can be combined with the corresponding extracted skeleton FIG. 220 as a part of the corresponding skeleton sequence 212 output. More detail of face-detection module 206 and face-recognition module 208 is described in U.S. patent application Ser. No. 16/672,432, filed on 2 Nov. 2019 and entitled "METHOD AND SYSTEM FOR PRIVACY-PRESERVING FALL DETECTION," the content of which is incorporated herein by reference.

Note that the generated skeleton sequence 212 can replace the actual images of the detected person in the raw video frames 230 for transmission, storage, and further action-recognition on cloud server 104. By transmitting the extracted skeleton sequences instead of transmitting the actual video images, the disclosed joint human-action recognition system 100 achieves a significantly lower network bandwidth requirement. Moreover, by storing the skeleton sequences of the detected persons instead of storing actual person images, the disclosed joint human-action recognition system 100 achieves a significantly reduced storage requirement and cost on cloud server 104. Furthermore, by using the preprocessed skeleton sequences of the detected persons to perform complex action recognition on cloud server 104 instead of using the raw person images, the disclosed joint human-action recognition system 100 achieves a significantly faster action recognition speed on cloud server 104.

As described above, deep-learning subsystem 106 is configured to separately capture (e.g., before capturing raw video frames 230) a background image of the monitored space/area without any person in the image. After raw video frames 230 are captured, deep-learning subsystem 106 is used to extract the skeleton sequences 212 of one or more detected persons from raw video frames 230. Next, the extracted skeleton sequences 212 can be transmitted to cloud server 104 along with the background image. Note that this background image only needs to be transmitted to cloud server 104 once, until the background image is updated on local vision sensor 102. Because the transmitted skeleton sequences 212 of the detected persons and the background image do not include any PII, the privacy of the detected persons is preserved and protected in the disclosed joint human-action recognition system 100. Note that at a later time, the recorded scene/action sequences in the captured video frames can be reconstructed on cloud server 104 by overlaying the extracted one or more skeleton sequences onto the background image in each reconstructed video frame to form a new video clip.

Note that while the joint human-action recognition system 100 of FIG. 1 shows a single local vision sensor 102, the disclosed joint human-action recognition system can generally include multiple local vision sensors that are all coupled to cloud server 104 through a network. Moreover, these multiple local vision sensors operate independently to capture raw video data and perform the above-described raw-video-data pre-processing to extract respective skeleton sequences of detected people from the respective raw video data in the respective monitoring location/area. The multiple sources/channels of the skeleton sequences and the respective background images of the respective monitoring locations/areas are subsequently transmitted to and received by cloud server 104. Because each vision sensor in the multiple local vision sensors includes a separate camera for capturing separate raw video data, a given channel of the skeleton sequences generated by a given vision sensor in the multiple local vision sensors can be differentiated from other channels of skeleton sequences by a unique camera ID of the camera on the given vision sensor or a unique group ID associated with a different group of people being monitored at a unique location/area.

Figure 4:
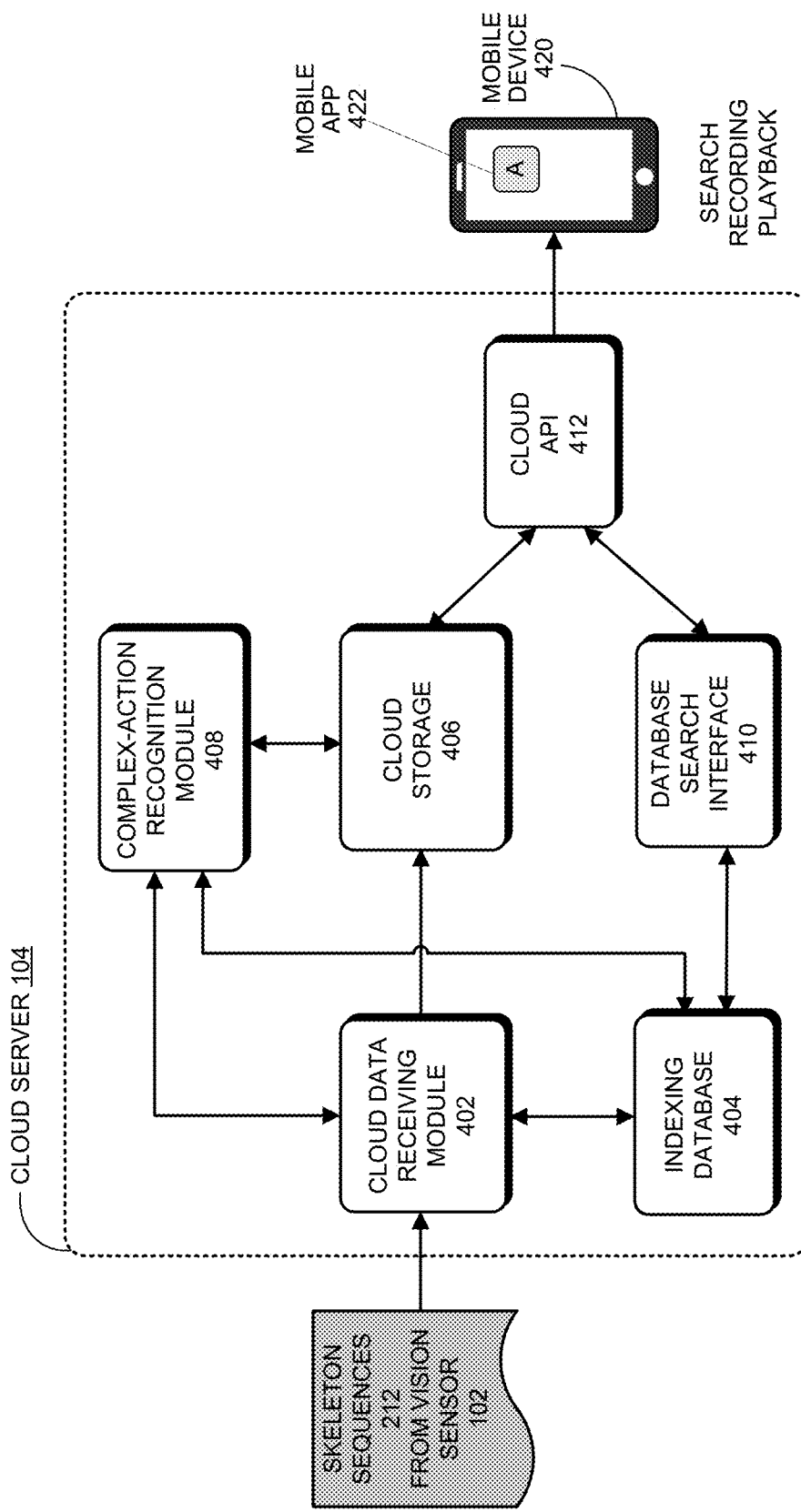
FIG. 4 shows a block diagram of the disclosed cloud server of the disclosed joint human-action recognition system in accordance with some embodiments described herein.

FIG. 4 shows a block diagram of disclosed cloud server 104 within the disclosed joint human-action recognition system 100 in accordance with some embodiments described herein. As can be seen in FIG. 4, cloud server 104 can include: a cloud-data receiving module 402, an indexing database 404, a cloud storage 406, a complex-action recognition module 408, a database search interface 410, and a cloud Application Programming Interface (API) 412. More specifically, cloud-data receiving module 402 of cloud server 104 receives pre-processed privacy-preserving skeleton sequences 212 from local vision sensor 102 as input. In some embodiments, cloud-data receiving module 402 is further configured to re-organize the received skeleton sequences 212, including indexing the received skeleton sequences 212 based on one or more data attributes. These data attributes that can be used to index the received skeleton sequences 212 can include, but are not limited to: action labels 214, people IDs 216, camera IDs (for embodiments of multiple local vision sensors), group IDs (e.g., people that belong to different monitoring groups), and recording timestamps. For example, cloud-data receiving module 402 can re-organize the received skeleton sequences 212 based on different people IDs, different group IDs, and/or different camera IDs. After data indexing, cloud-data receiving module 402 is configured to store the indexing tables and pointers of the skeleton-sequence data into indexing database 404 for advanced searches, queries, data processing by an external user App or by an internal data-processing module such as complex-action recognition module 408. Note that storing indexing tables and pointers of the received skeleton sequences 212 into indexing database 404 allows for fast searching and queries without the need to scan the entire skeleton-sequence database.

In some embodiments, in addition to storing the indexed skeleton sequences into indexing database 404, cloud-data receiving module 402 is also configured to store originally-received skeleton sequences 212 into cloud storage 406 without any modification. In some embodiments, the non-modified skeleton sequences are stored in cloud storage 406 encrypted. Moreover, the stored skeleton-sequence data can be separated in cloud storage 406 by the camera IDs, group IDs, people IDs, and record timestamps. In some embodiments, cloud storage 406 is implemented as a mass storage. Note that storing extracted skeleton-sequences data in place of raw video images provides an extremely low-cost and privacy-preserving option for users who have need to store many hours of the recorded human action data temporarily or permanently.

In some embodiments, database search interface 410 in cloud server 104 is configured to process search requests to indexing database 404 from external user devices, such as a search request generated by a mobile App 420 installed on a mobile device 422. More specifically, database search interface 410 is configured to process search requests from mobile App 422 through Cloud API 412, and the processed requests are used to query the stored indexed-skeleton-sequence data in indexing database 404. In some embodiments, when the search request has been processed, only the stored skeleton-sequence data starting from the requested timestamp in the query request is retrieved from cloud stage 406 and sent to the mobile App 420 through cloud API 412 for playback. In this manner, data transfer costs can be significantly reduced.

Using the disclosed joint human-action recognition system 100, sanitized/de-identified skeleton sequences 212 can be generated locally on the local vision sensor 102 and transmitted to cloud server 104 in place of the raw video images to preserve the privacy of each monitored person. In some embodiments, complex-action recognition module 408 in cloud server 104 is configured to perform either real-time or offline complex action recognition based on the received skeleton sequences 212. In some embodiments, for real-time action recognition, complex-action recognition module 408 can directly receive real-time skeleton sequences 212 from cloud-data receiving module 402, and subsequently process the received skeleton sequences 212 to generate complex action/activity predictions using deep-learning techniques and big-data analytics. These complex actions/activities can include, but are not limited to: eating, cooking, quality of service of care workers, or diagnosis of certain behavioral diseases such as dementia, Parkinson's, and depression. Because cloud server 104 includes significantly higher computational resources and storage space than local vision sensor 102, complex-action recognition module 408 on cloud server 104 is able to comfortably process real-time skeleton sequences 212 using high-complexity deep-learning algorithms and big-data analytics for any number of detected people and generate real-time human action/activity predictions based on the real-time skeleton sequences 212. Consequently, local vision sensor 102 and cloud server 102 operate collectively and concurrently to achieve privacy-preserving complex human action recognitions for multiple detected people in real-time.

Alternatively, complex-action recognition module 408 can be configured to perform offline complex action recognition that requires long-term data from received skeleton-sequence data 212. More specifically, complex-action recognition module 408 can retrieve stored indexed skeleton sequences from indexing database 404 and cloud storage 406 at a later time based on an external action recognition request from mobile App 422. Complex-action recognition module 408 subsequently processes the retrieved skeleton sequences from indexing database 404 to generate complex action/activities predictions.

In some embodiments, the disclosed joint human-action recognition system 100 is configured to play back a skeleton sequence stored on cloud server 104 associated with a detected person from a raw video. As described above, this extracted and stored skeleton sequence represents a continuous human motion corresponding to a sequence of video frames or an entire recorded video. In some embodiments, the skeleton sequence playback request can be issued by mobile App 422 on mobile device 420. More specifically, the playback request can specify a person ID and a starting timestamp for a stored skeleton sequence of a particular person identified by the person ID. The playback request can also specify a camera ID and a starting timestamp for the stored skeleton sequences of all persons captured by the particular local vision sensor. The playback request can also specify a time-duration for the playback, so that a precise portion of the stored skeleton sequences can be retrieved from the cloud storage. In some embodiments, to reconstruct a video segment, the retrieved skeleton sequence can be overlaid onto a corresponding identical background image in each reconstructed video frame. Note that this skeleton-sequence-playback function of the disclosed joint human-action recognition system 100 creates a motion animation of the extracted skeleton figures of the detected person, which allows for visualizing and recognizing the action and/or behavior of the person without showing actual body and face of the detected person. Note that, during the skeleton-sequence playback, the name of the detected person can be displayed alongside the animation sequence to differentiate different detected people and difference displayed skeleton sequences.

Figure 5:
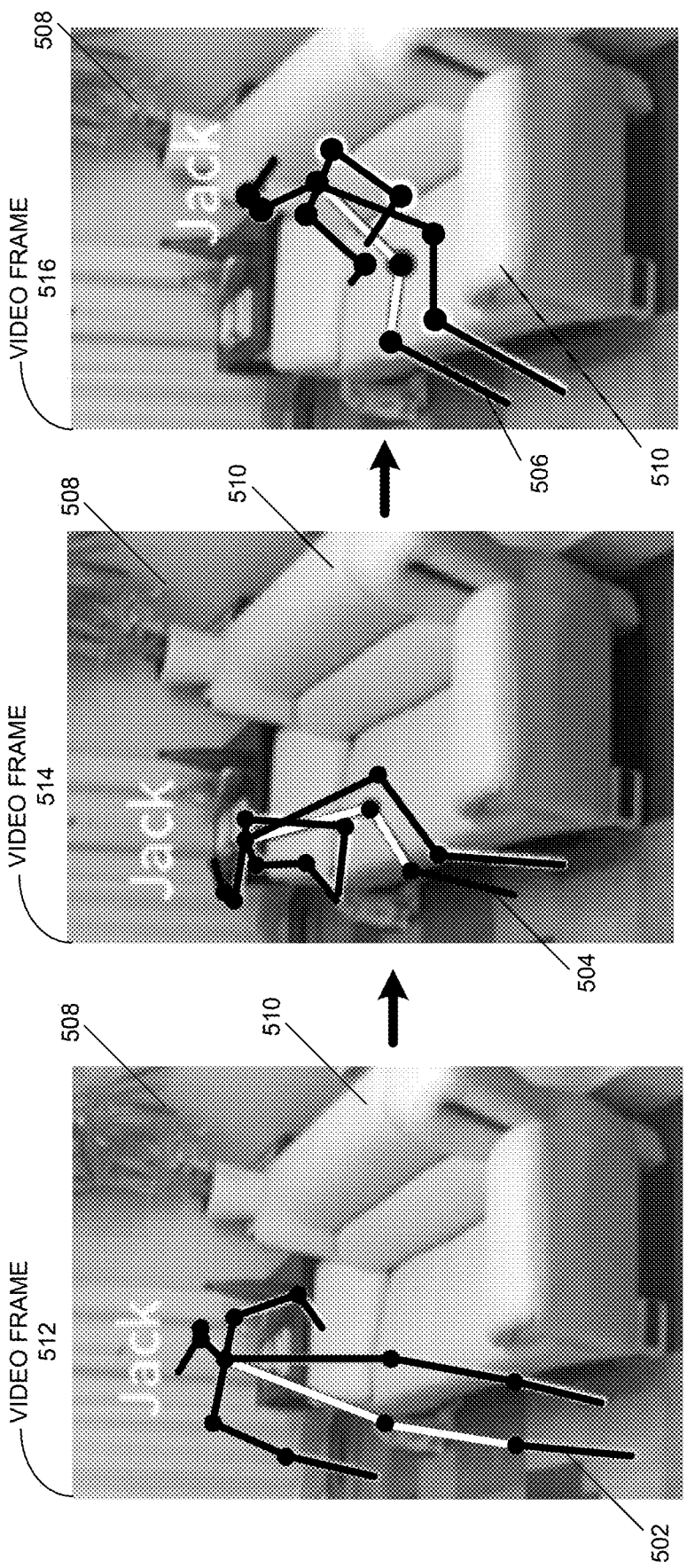
FIGS. 5A-5C show an exemplary reconstruction and playback application of a skeleton sequence of a detected person in front of a common background image in accordance with some embodiments described herein.

FIGS. 5A-5C show an exemplary reconstruction and playback application of a skeleton sequence 500 of a detected person "Jack" in front of a common background image 508 in accordance with some embodiments described herein. Note that each of the figures FIG. 5A, FIG. 5B, and FIG. 5C includes an extracted skeleton FIGS. 502, 504, and 506, respectively of the same person in a different pose, corresponding to an action/pose at a particular timestamp within a continuous sequence of movements. The sequence of skeleton FIGS. 502, 504, and 506 forms the skeleton sequence 500. Moreover, each of FIGS. 5A-5C also includes an identical background image 508 including a sofa 510. The skeleton sequence 500 combined with background image 508 form a sequence of reconstructed video frames 512, 514, and 516 which can be played back. As described above, the sequence of video frames 512, 514, and 516 corresponding to the skeleton sequence 500 be reconstructed by simply overlaying each skeleton FIG. 502-506 onto the static background image 508 (which can be separately recorded and stored) at the exact location where the corresponding skeleton figure was originally identified and extracted.

In the exemplary reconstructed skeleton sequence 500, a continuous sequence of movements of a person from standing in front sofa 510 to sitting down on sofa 510 is displayed using the corresponding skeleton figures without showing actual face or even the actual body of the person, thereby fully preserving and protecting the privacy of the person. Instead, the person associated with the skeleton sequence 500 can be identified with a labeled/person ID as such "Jack," indicating all three skeleton FIGS. 502, 504, and 506 belong to the same person. More specifically, the exemplary skeleton sequence 500 begins with "Jack" standing in front of sofa 510 in FIG. 5A, which is followed by "Jack" in a crouching/squatting pose over sofa 510 in FIG. 5B, and finally when "Jack" in a fully-sitting-down pose on sofa 510 in FIG. 5C. Note that although the three skeleton FIGS. 502-506 in exemplary skeleton sequence 500 are all labeled with the same name/person ID, they may also have different names/person IDs if these skeleton figures do not belong to the same person. Hence, the displayed name/person ID to each skeleton figure is highly important to differentiate different people when all face images are removed. Note that although exemplary skeleton sequence 500 includes only three reconstructed video frames, other embodiments of a skeleton sequence showing the same or a similar sequence of movements can include significantly more intermediate skeleton figures/frames between video frame 512 and video 514.

In some embodiments, the disclosed joint human-action recognition system 100 is configured to use the extracted skeleton figures and/or a skeleton sequence of a detected person in different video frames to detect some complex actions, such as eating, cooking, or detect some behavioral diseases, such as Parkinson's disease, dementia, and depression. Note that these functions can be performed by complex action-recognition module 408 within the cloud server 104 of the disclosed joint human-action recognition system 100 to generate alarms/alerts or notifications.

In some embodiments, the disclosed joint human-action recognition system 100 is configured to perform face detection of each detected person in the input video frames 230, and label a detected person with an associated personal ID if the face is recognized in a face database of the disclosed local visual sensor 102 (not shown). Note that these face-detection and recognition functions can be performed by face detection module 206 and face recognition module 208 within deep-learning subsystem 106 of local vision sensor 102 of the disclosed joint human-action recognition system 100, which includes generating and output people IDs 216.

In some embodiments, the disclosed joint human-action recognition system 100 is further configured to extract important subimages from the input video frames 230, such as the face of a detected person, or a part/entire body of a detected person, which can be useful for some applications, such as surveillance. Note that these functions can be performed by face detection module 206 within deep-learning subsystem 106 of local vision sensor 102 to generate extracted face subimages and by pose estimation module 202 within deep-learning subsystem 106 of local vision sensor 102 to generate and output extracted human body subimages. In some embodiments, the extracted face subimages and extracted human body subimages can also be transmitted to cloud server 104 for storage and post-processing, for example, to investigate the identities of strangers that are not recognized by the local vision sensor.

Figure 6:
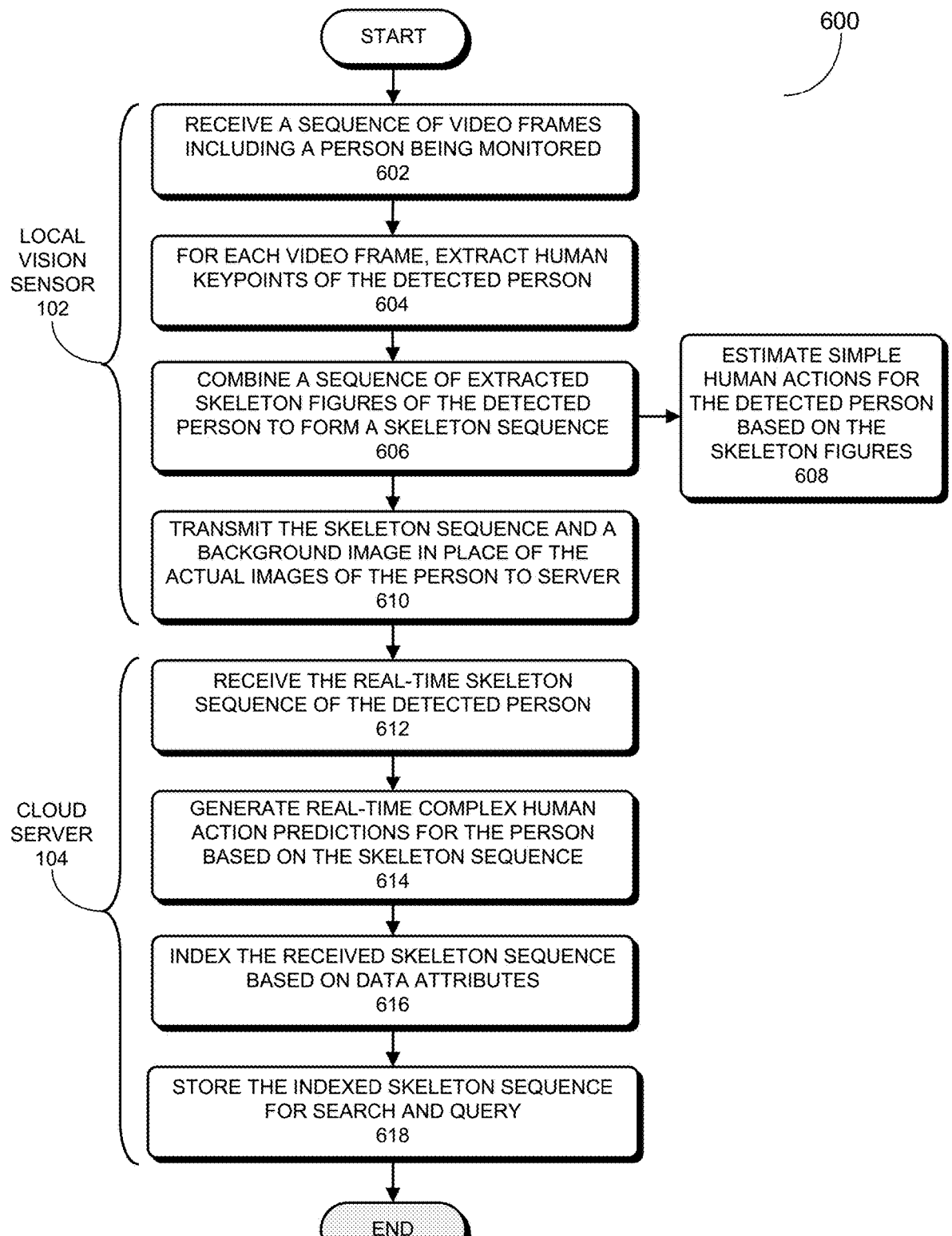
FIG. 6 presents a flowchart illustrating an exemplary process for performing real-time human-action recognition using the disclosed joint human-action recognition system in accordance with some embodiments described herein.

FIG. 6 presents a flowchart illustrating an exemplary process for performing real-time human-action recognition using the disclosed joint human-action recognition system 100 in accordance with some embodiments described herein. In one or more embodiments, one or more of the steps in FIG. 6 may be omitted, repeated, and/or performed in a different order. Accordingly, the specific arrangement of steps shown in FIG. 6 should not be construed as limiting the scope of the technique.

Process 600 may begin by receiving a sequence of video frames including a person being monitored (step 602). For example, the sequence of video frames may be captured by a camera installed at an assisted living facility or a nursing care home, and the one or more persons being monitored can be elderly people living in the assisted living facility or the nursing care home. Next, for each video frame in the sequence of video frames, process 600 detects the person in the video frame, and subsequently extracts a set of human keypoints of the detected person from the detected person image (step 604). Note that process 600 performs step 604 locally on a local vision sensor/smart camera where the sequence of video frames are captured. For example, process 600 can used the above described pose estimation module 202 to perform person detection and human keypoint extraction. Process 600 subsequently combines a sequence of extracted skeleton figures of the detected person extracted from the sequence of video images to form a skeleton sequence of the detected person which depicts a continuous motion of the detected person (step 606). Note that process 600 performs step 606 locally on the local vision sensor/smart camera where the sequence of video frames are captured.

Process 600 next estimates some simple human actions for the detected person based on the sequence of extracted skeleton figures (step 608). For example, process 600 can perform a deep-learning-based action recognition based on the configuration of each set of extracted human keypoints and/or localizations of the associated set of keypoints, and subsequently generate an action label for the detected person in each video frame. As described above, the types of simple human actions that can be predicated at step 608 can include standing, sitting down, lying down, fall detection, and waving hand detection. Note that process 600 performs step 608 locally on the local vision sensor/smart camera where the sequence of video frames are captured. For example, process 600 can used the above described simple-action recognition module 204 to perform these simply human action estimations. In some embodiments of process 600, step 608 is an optional step.

Next, process 600 transmits the skeleton sequence of the detected person and a background image common to the sequence of video frames in place of the actual images of the detection person from the local vision sensor to a cloud server (step 610). Note that process 600 does not transmit the actual images of the detected person to the cloud server, and the transmitted skeleton sequence of the detected person and the background image do not include any PII. Consequently, the privacy of the detected person is preserved and protected during the human action data transmission of step 610. Note that all steps 602-610 take place in real-time as the detected person is being monitored.

Next, process 600 receives the real-time skeleton sequence of the detected person at the cloud server (step 612). Process 600 subsequently generates real-time complex human action predictions for the detected person based on the received skeleton sequence using deep-learning techniques and big-data analytics (step 614). As described above, these complex human actions can include eating, cooking, certain manners of falling, or diagnosis of certain behavioral diseases such as dementia, Parkinson's, and depression. Note that process 600 performs step 612 on the cloud server, e.g., using complex action recognition module 408, which includes significantly higher computational resources and storage space than the local vision sensor where the original video frames are captured. Process 600 subsequently re-organizes the received skeleton sequence by indexing the received skeleton sequence based on one or more data attributes (step 616). These data attributes that can be used to index the received skeleton sequence can include, but are not limited to: people IDs, camera IDs, group IDs (e.g., people that belong to different monitoring groups), and recording timestamps. Process 600 then stores the indexed skeleton sequence into an indexing database so that the newly-received skeleton sequence can be efficiently searched, queried, and post-processed by various user applications (step 618). Consequently, process 600 uses the local vision sensor and the cloud server jointly and concurrently to achieve privacy-preserving complex human action recognitions for the detected people in real-time.

Figure 7:
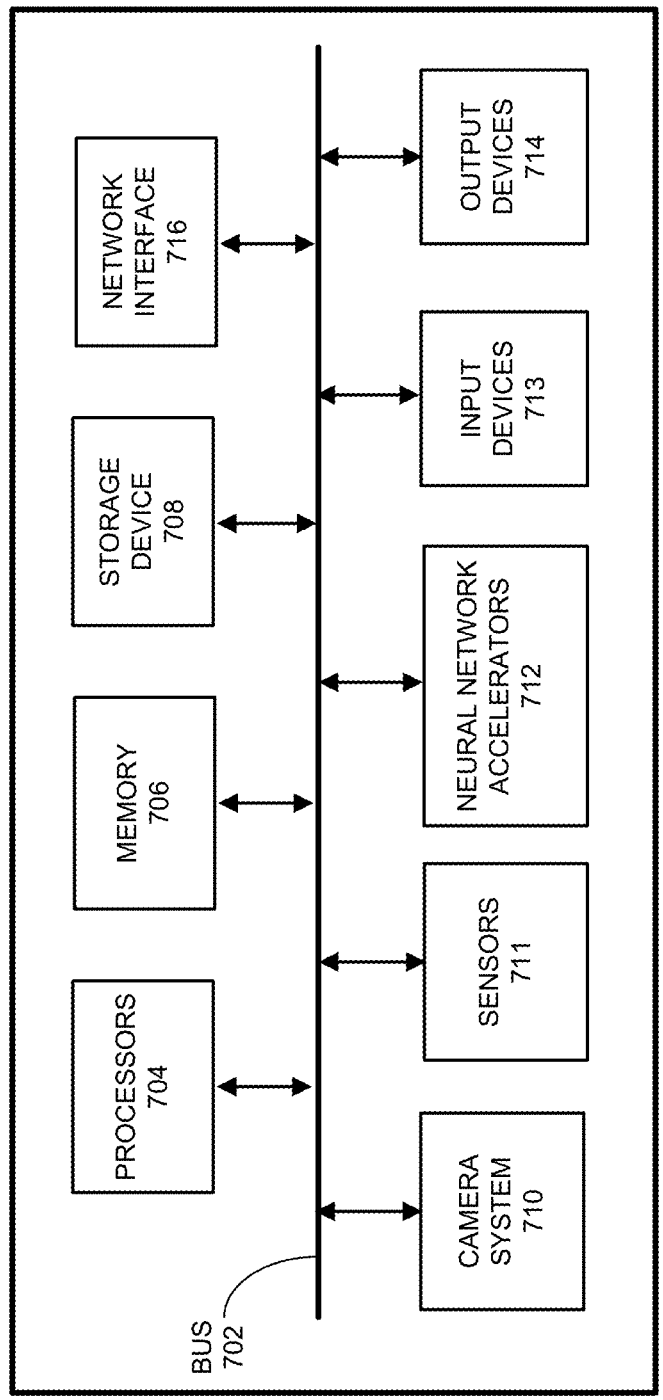
FIG. 7 illustrates an exemplary hardware environment for the disclosed local vision sensor in the disclosed joint human-action recognition system in accordance with some embodiments described herein.

FIG. 7 illustrates an exemplary hardware environment 700 for the disclosed local vision sensor 102 in the disclosed joint human-action recognition system 100 in accordance with some embodiments described herein. As can be seen in FIG. 7, hardware environment 700 can include a bus 702, one or more processors 704, a memory 706, a storage device 708, a camera system 710, sensors 711, one or more neural network accelerators 712, one or more input devices 713, one or more output devices 714, and a network interface 716.

Bus 702 collectively represents all system, peripheral, and chipset buses that communicatively couple the various components of hardware environment 700. For instance, bus 702 communicatively couples processors 704 with memory 706, storage device 708, camera system 710, sensors 711, neural network accelerators 712, input devices 713, output devices 714, and network interface 716.

From memory 706, processors 704 retrieves instructions to execute and data to process in order to control various components of hardware environment 700, and to execute various functionalities described in this patent disclosure including the various disclosed functions of the various functional modules in the disclosed deep-learning subsystem 106, including but not limited to: pose-estimation module 202, simple-action recognition module 204, face-detection module 206, and face-recognition module 208. Processors 704 can include any type of processor, including, but not limited to, one or more central processing units (CPUs), one or more microprocessors, one or more graphic processing units (GPUs), one or more tensor processing units (TPUs), one or more digital signal processors (DSPs), one or more field-programmable gate arrays (FPGAs), one or more application-specific integrated circuit (ASICs), a personal organizer, a device controller and a computational engine within an appliance, and any other processor now known or later developed. Furthermore, a given processor 704 can include one or more cores. Moreover, a given processor 704 itself can include a cache that stores code and data for execution by the given processor 704.

Memory 706 can include any type of memory that can store code and data for execution by processors 704, neural network accelerators 712, and some other processing modules of hardware environment 700. This includes but not limited to, dynamic random access memory (DRAM), static random access memory (SRAM), flash memory, read only memory (ROM), and any other type of memory now known or later developed.

Storage device 708 can include any type of non-volatile storage device that can be integrated with hardware environment 700. This includes, but is not limited to, magnetic, optical, and magneto-optical storage devices, as well as storage devices based on flash memory and/or battery-backed up memory. In some implementations, various programs for implementing the various disclosed functions of the various disclosed modules in the disclosed deep-learning subsystem 106 of local vision sensor 102, including but not limited to: pose-estimation module 202, simple-action recognition module 204, face-detection module 206, and face-recognition module 208, are stored in memory 706 and storage device 708.

Bus 702 is also coupled to camera system 710. Camera system 710 is configured to capture a sequence of video images at predetermined resolutions and couple the captured video images to various components within hardware environment 700 via bus 702, such as to memory 706 for buffering and to processors 704 and neural network accelerators 712 for various deep-learning and neural network-based operations. Camera system 710 can include one or more digital cameras. In some embodiments, camera system 710 includes one or more digital cameras equipped with wide-angle lenses. The captured images by camera system 710 can have different resolutions including high-resolutions such as at 1280×720p, 1920×1080p or other high resolutions.

In some embodiments, neural network accelerators 712 can include any type of microprocessor designed as hardware acceleration for executing AI-based and deep-learning-based programs and models, and in particular various deep learning neural networks such as various CNN and RNN frameworks mentioned in this disclosure. Neural network accelerators 712 can perform the intended functions of each of the described deep-learning-based modules within the disclosed deep-learning subsystem 106 of local vision sensor 102, including but not limited to: pose-estimation module 202, simple-action recognition module 204, face-detection module 206, and face-recognition module 208. Examples of neural network accelerators 712 can include but are not limited to: the dual-core ARM Mali-G71 GPU, dual-core Neural Network Inference Acceleration Engine (NNIE), and the quad-core DSP module in the HiSilicon Hi3559A SoC.

Bus 702 also connects to input devices 713 and output devices 714. Input devices 713 enable the user to communicate information and select commands to hardware environment 700. Input devices 713 can include, for example, a microphone, alphanumeric keyboards and pointing devices (also called "cursor control devices").

Hardware environment 700 also includes a set of sensors 711 coupled to bus 702 for collection environment data in assisting various functionalities of the disclosed local vision sensor 102. Sensors 711 can include a motion sensor, an ambient light sensor, and an infrared sensor such as a passive infrared sensor (PIR) sensor. To enable the functionality of a PIR sensor, hardware environment 700 can also include an array of IR emitters.

Output devices 714 which are also coupled to bus 702, enable for example, the display of the results generated by processors 704 and neural network accelerators 712. Output devices 714 include, for example, display devices, such as cathode ray tube displays (CRT), light-emitting diode displays (LED), liquid crystal displays (LCD), organic light-emitting diode displays (OLED), plasma displays, or electronic paper. Output devices 714 can also include audio output devices such as a speaker. Output devices 714 can additionally include one or more LED indicators.

Finally, as shown in FIG. 7, bus 702 also couples hardware environment 700 to a network (not shown) through a network interface 716. In this manner, hardware environment 700 can be a part of a network, such as a local area network ("LAN"), a Wi-Fi network, a wide area network ("WAN"), or an Intranet, or a network of networks, such as the Internet. Hence, network interface 716 can include a Wi-Fi network interface. Network interface 716 can also include a Bluetooth interface. Any or all components of hardware environment 700 can be used in conjunction with the subject disclosure.

Note that while we have described various embodiments of the joint human-action recognition system 100 based on using human skeleton/keypoint representations, the general concept of performing human action recognitions, transmitting, storing and retrieving human action sequences using a type of privacy-preserving human representation/data format is not limited to just human skeleton/keypoint representation/data format. In various other embodiments of the joint human-action recognition system 100, the raw videos can also be converted to another type of privacy-preserving data format other than the human skeleton/keypoint data format. These alternative privacy-preserving data formats that can be used in the disclosed joint human-action recognition system 100 in place of the human skeleton/keypoint data format to represent a detected person can include, but are not limited to: a 3D mesh of human body; a human outline (e.g., mask, silhouette, or 3D mesh) representation of a human body; thermal images of a detected person; depth maps of a detected person generated by depth cameras; and human body representation by other radar sensors (e.g., millimeter wave sensors).

Note that when using an alternative privacy-preserving data format, such as a human outline format in place of the above-described human skeleton/keypoint data format in the disclosed joint human-action recognition system 100, the disclosed local vision sensor is configured to convert the detected persons in the raw video images into this alternative privacy-preserving data format, and perform simple action recognition such as fall detection on the disclosed local vision sensor. The disclosed local vision sensor is further configured to transmit a converted/extracted human-action sequence data in the alternative privacy-preserving data format in place of the raw person images to the cloud server, thereby fully preserving and protecting the privacy of the detected person. On the cloud server, the human-action sequence data in the alternative privacy-preserving data format can be further processed (e.g., to perform complex action recognitions), indexed, stored, later retrieved, and played back at a later time in similar manners as described-above in the scope of the human skeleton/keypoint data format.

Low-Cost Storage of Skeleton Sequences

As described above, the disclosed smart visual sensor 102 is configured to extract and transmit the skeleton sequence of a detected person from a sequence of raw video frames in real time when a video is being captured. In some embodiments, the extracted skeleton sequences by the disclosed smart visual sensor 102 can be stored in place of the raw video frames from which the skeleton sequences are extracted. A person of ordinary skill can appreciate that only a very small amount of storage space is needed to store the disclosed structured human action sequence data, i.e., the skeleton figures/skeleton sequences compared to saving the raw video images/videos.

For example, if 18 keypoints are used to represent a single skeleton figure, each keypoint in the set of keypoints can be represented by an associated body joint index, 2D or 3D coordinates, and a probability value as described above. Moreover, each extracted skeleton figure can be associated with additional labels and properties. For example, these additional labels and properties can include a recognized action label (by simple-action recognition module 204) and the corresponding probability. When combined, each extracted skeleton figure in the disclosed skeleton sequence will require less than 250 bytes to represent all the information. The size of skeleton-figure data can be further reduced by using certain existing lossless compression techniques, which can easily reduce the required storage space by additional 50% or more.

Using the maximum byte size of 250, if the frame rate of the recorded skeleton sequence is 10-frame/second, then the data rate can be reduced to 2500 bytes/sec per recorded person. As such, one hour of the recorded skeleton sequence will only have 9 MB data size, which is merely 2% of the typical 360p video storage requirement, and 0.4% of the 720p video storage requirement mentioned above. Even if the frame rate of the recorded video is scaled up to 25-fps which is the recommended frame rate of YouTube videos, the storage requirement of the disclosed skeleton sequence is still only 5% of the 360p video storage requirement, and 1% of the 720p video storage requirement. Note that all of above comparisons are made without applying any compression to the recorded skeleton sequence.

Using the disclosed smart visual sensor 102 and the disclosed skeleton sequence extraction and storage techniques, assuming a person being monitored is active for 16 hours each day, the captured skeleton sequence data will have a size of at most 9×16=144 MB/day (using 250-byte/figure as upper limit), or 4.32 GB/month. This suggests that the associated monthly storage cost/monitored person is only about $0.1 (using common commercial cloud storage pricing). In comparison, a 30-day subscription fee for common video storage is $30 from a well-known video surveillance company. Note that a direct consequence of a significantly reduced per-person monthly storage/storage cost requirement is that, for the same storage duration, the disclosed structured human-action data offer much lower monthly storage cost. Alternatively, for the same monthly storage cost, the disclosed structured human-action data would allow a much longer storage time, and even life-long data storage can become possible.

Applications Based on Structured Skeleton-Sequence Data

Note that because the storage of the skeleton sequences of the detected persons generated by the disclosed joint human-action recognition system 100 is only a few percentage (%) of that of the raw/original video data, it becomes very affordable to any user to store the extracted skeleton sequences of full videos (not just some short event clips) in place of the original videos for a much longer storage time in the server, without violating people's privacy (because no actual face images are transmitted and stored). For example, for the same storage duration, using the disclosed joint human-action recognition system 100 and the disclosed skeleton-sequence data structure can result in much lower storage spaces and monthly storage costs. Alternatively, for the same monthly fee, a user can be provided with much longer storage time, even life-long data storage is possible.

Note that the disclosed joint human-action recognition system 100 integrates the functions of three types of conventional medical systems: a medical alert system; a surveillance video system; and a telemedicine system.

Note that storing skeleton figures/sequences in place of original images of the detected persons can result in a very small amount of data being stored for the detected persons. The stored skeleton figures/sequences of a large number of detected people can be used to construct a skeleton figures/sequences database, and searching through such a skeleton figures/sequences database can be extremely fast. In an exemplary mobile App of the disclosed joint human-action recognition system 100 that implements such a skeleton figures/sequences database, users can search through the stored skeleton data, play back the desired skeleton sequences/clips at a specified date, time, and location, or play back the skeleton sequence of a person at a specified date and time.

In some surveillance applications, both the extracted structured skeleton data and (1) face or (2) human body subimages extracted from the original video images can be stored on the server. By combining the structured skeleton data with one of (1) face and (2) human body subimages, the proposed surveillance systems based on the disclosed joint human-action recognition system 100 can achieve a good tradeoff between preserving important identifiable personal information (e.g., based on face or human body subimages) and reducing the server storage.

Some mobile app implementations of the disclosed joint human-action recognition system 100 can also provide certain useful statistics based on the output data of the disclosed joint human-action recognition system 100. For example, an exemplary mobile app can include a heat map function for visualizing how long a detected person spends in each area of the home.

Note that because entire skeleton sequences of the detected persons from an original video can be stored in cloud server 104, even if the emergency detection functions on the disclosed local vision sensor 102 fail to detect certain emergency events, the stored skeleton sequences of the detected persons can still be used to help the event analysis and review afterwards on cloud server 104.

Some mobile App implemented for the disclosed joint human-action recognition system 100 can also include an API that can be integrated with popular Electronic Medical Record (EMR) platforms used by many hospitals and healthcare facilities. This API provides a portal to the EMR platforms to access a new type of valuable patient data—the daily human action skeleton data. Through the API function of the disclosed mobile App implementations, the disclosed local vision sensor 102 becomes a useful new medical device for doctors and patients. The doctors can use the skeleton figure/sequence data generated by the disclosed local vision sensor 102 to observe the behaviors of patients from their home, e.g., to collect information such as how many times a given patient goes to the kitchen and eats each day, or if another patient sits at one location for a long period of time. Note that even if these patients cannot provide accurate feedback by themselves, skeleton figure/sequence data collected remotely and automatically for these patients can be used to evaluate the efficiency of the treatments or rehabilitations for many diseases, such as dementia, Parkinson's disease, depression, autism, mental diseases, and other conduct disorders, and subsequently adjust the treatments based on the evaluation results.

The disclosed structured human-action/skeleton data can also be used by other organizations in additional medical application. For example, senior care facilities and home care companies can use the disclosed structured human-action/skeleton data to provide care to seniors. Insurance companies can use the disclosed structured human-action/skeleton data to evaluate the health condition of a given person and determine proper insurance premiums for the given person. Insurance companies and the governments can also use the disclosed structured human-action/skeleton data to evaluate the quality of services provided by home care workers for seniors or patients that require home cares, and subsequently determine a proper payment level to the care workers. Furthermore, pharmaceutical companies can use the disclosed structured human-action/skeleton data to evaluate the efficacy of new drugs that they've developed. Moreover, university researchers can use the disclosed joint human-action recognition system 100 to perform a wide range of medical researches.

In addition to the aforementioned recording, extraction, storage and playback functionalities, various big-data analytics functionalities can be developed based on the skeleton sequence data collected by the disclosed local vision sensor 102 and stored on the server. For example, advanced machine learning models can be trained to perform some inference tasks on the stored skeleton sequence data, e.g., for early diagnosis of certain conditions from the skeleton data, such as dementia and Parkinson's. Note that such early diagnoses can be crucial to the early treatment, and are beneficial for patients and their families, because they can result in substantial cost savings to the patients and the healthcare systems.

Note that the abilities to perform various aforementioned medical applications without violating the privacy of the people being monitored can be especially useful in the wake of COVID-19 pandemic, as a growing number of people are choosing to use telemedicine technologies.

Alternative Skeleton Data Solutions

In some application cases, traditional surveillance video camera systems are already in use, which could be expensive to replace with the disclosed smart vision sensors such as local vision sensor 102. In such cases, to reduce the storage cost at the server, the raw videos can be first uploaded to the cloud server by these traditional systems. Subsequently at the cloud server, the disclosed structured skeleton data extraction and other functionalities described in conjunction with FIGS. 1-2 can be used to extract the structured skeleton data, which are then stored on the cloud server. The original uploaded video can then be deleted from the server. Note that this hybrid approach can also reduce the storage cost at the server, but it would still need the same uploading bandwidth as for uploading traditional surveillance videos, and does not provide the same level of user privacy protection as the disclosed local vision sensor 102.

Another option is to install a local server or hub that includes a copy of the disclosed local vision sensor 102 in a facility or a house, which is connected to the stored traditional surveillance videos in the facility or the house by wired or wireless networks. The raw videos recorded by traditional cameras can be converted to skeleton sequences by the disclosed local vision sensor, and the skeleton sequences are then transmitted to the cloud server for long-term storage and analysis. The disclosed local server can be implemented with a desktop computer, or alternatively implemented by a powerful embedded device. After generating the skeleton sequences, the original surveillance videos can be deleted, or kept in the disclosed local server for some time, until the hard disk of the local server is full. At this point, the local server can overwrite old videos with newly recorded videos. This process can also protect the privacy of the users because the original videos are not sent to the cloud server.

While this patent document contains many specifics, these should not be construed as limitations on the scope of any invention or of what may be claimed, but rather as descriptions of features that may be specific to particular embodiments of particular inventions. Certain features that are described in this patent document and attached appendix in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document and attached appendix should not be understood as requiring such separation in all embodiments.

Only a few implementations and examples are described and other implementations, enhancements and variations can be made based on what is described and illustrated in this patent document and attached appendix.

What is claimed is:

1. A method of managing human motion data, comprising:
   receiving a sequence of video images including at least a first person;
   for each video image in the sequence of video images,
      detecting the first person in the video image; and
      extracting a skeleton figure of the detected first person from the detected image of the first person, wherein the skeleton figure is composed of a set of human keypoints of the detected first person;
   combining a sequence of extracted skeleton figures of the detected first person from the sequence of video images to form a first skeleton sequence of the detected first person, wherein the first skeleton sequence depicts a continuous motion of the detected first person; and transmitting the first skeleton sequence of the detected first person along with a common background image associated with the sequence of video images to a server to be stored on the server, wherein the common background image is transmitted only once, wherein transmitting the first skeleton sequence of the detected first person and a single copy of the common background image in place of the detected images of the first person to the server preserves the privacy of the detected first person.

2. The method of claim 1, wherein the method further comprises:
for each video image in the sequence of video images, detecting a second person in the video image; and
extracting a skeleton figure of the detected second person from the detected image of the second person, wherein the skeleton figure is composed of a set of human keypoints of the detected second person;
combining a sequence of extracted skeleton figures of the detected second person from the sequence of video images to form a second skeleton sequence of the detected second person, wherein the second skeleton sequence depicts a continuous motion of the detected second person; and
transmitting the second skeleton sequence of the detected second person to the server to be stored on the server, wherein transmitting the second skeleton sequence of the detected second person in place of the detected images of the second person to the server significantly reduces both transmission bandwidth requirements and storage space requirements on the server.

3. The method of claim 2, wherein the method further comprises:
transmitting a first person ID of the detected first person along with the first skeleton sequence to the server;
transmitting a second person ID of the detected second person along with the second skeleton sequence of to the server; and
indexing the stored first skeleton sequence and second skeleton sequence in a skeleton sequence database on the server with the first person ID and the second person ID, respectively.

4. The method of claim 1, wherein each human keypoint in the set of human keypoints of the detected first person is specified by:
a keypoint index corresponding to a particular body joint;
either a two-dimensional (2D) location (i.e., a set of X- and Y-coordinates in a 2D plane), or a three-dimensional (3D) location (i.e., a set of X-, Y-, and Z-coordinates in a 3D space); and
a probability value associated with a prediction of the particular body joint.

5. The method of claim 1, wherein the method further comprises predicting a human action among various types of simple human actions associated with the sequence of video images based on the first skeleton sequence.

6. The method of claim 5, wherein the various types of simple human actions include: standing, sitting down, lying down, falling, and waving hand.

7. The method of claim 1, wherein the method further comprises:
obtaining the common background image, wherein the common background image does not include any person;
transmitting the common background image along with the first skeleton sequence of the detected first person to the server in place of the sequence of video images, wherein the first skeleton sequence and the common background image do not include any personal identifiable information (PII).

8. The method of claim 1, wherein the method further comprises:
receiving the first skeleton sequence of the detected first person at the server; and
predicting complex human actions associated with the sequence of video images based on the received first skeleton sequence at the server.

9. The method of claim 8, wherein the complex human actions include: eating, cooking, quality of service of care workers, or diagnosis of certain behavioral diseases comprising at least one of: dementia, Parkinson's, and depression.

10. The method of claim 8, wherein the complex human actions include those actions that need long-time data.

11. The method of claim 8, wherein the method further comprises creating a motion animation by playing back the first skeleton sequence of the detected first person, thereby allowing visualizing and recognizing the action of the detected first person without showing actual body and face of the detected first person.

12. The method of claim 11, wherein the method further comprises displaying an associated personal ID of the detected first person next to the motion animation.

13. The method of claim 1, wherein the method further comprises:
extracting a first sequence of face images of the detected first person from the sequence of video images; and
transmitting the first sequence of face images along with the first skeleton sequence of the detected first person in place of the detected images of the first person to the server for storage and post-processing.

14. The method of claim 1, wherein the method further comprises:
extracting a first sequence of human body images of the detected first person from the sequence of video images; and
transmitting the first sequence of human body images along with the first skeleton sequence of the detected first person in place of the detected images of the first person to the server for storage and post-processing.

15. The method of claim 1, wherein the storage space requirements for storing the first skeleton sequence of the detected first person on the server is less than 1% of the storage space requirements for storing the detected images of the first person.

16. The method of claim 1, wherein storing skeleton sequences of detected persons in place of the actual images of the detected persons from recorded videos on the server allows for storing full videos for significantly longer storage time on the server, without violating the privacies of the detected persons.

17. The method of claim 1, wherein storing skeleton sequences of detected persons in place of the actual images of the detected persons from recorded videos on the server allows for significantly reducing the monthly storage fees for a user.

18. The method of claim 1, wherein after transmitting the first skeleton sequence of the detected first person to the server, the sequence of video images are deleted.

19. A smart sensor that can extract a continuous human action skeleton sequence in real time and send the continuous human action skeleton sequence to a cloud server, the smart sensor comprising:

one or more cameras configured to capture a sequence of video images including at least a first person;
one or more processors; and
a memory coupled to the one or more processors and storing instructions that, when executed by the one or more processors, cause the smart sensor to:
receive the sequence of video images;
for each video image in the sequence of video images,
detect the first person in the video image; and
extract a skeleton figure of the detected first person from the detected image of the first person, wherein the skeleton figure is composed of a set of human keypoints of the detected first person;
combine a sequence of extracted skeleton figures of the detected first person from the sequence of video images to form a first skeleton sequence of the detected first person, wherein the first skeleton sequence depicts a continuous motion of the detected first person; and
transmit the first skeleton sequence of the detected first person along with a common background image associated with the sequence of video images to a server to be stored on the server, wherein the common background image is transmitted only once, wherein transmitting the first skeleton sequence of the detected first person and a single copy of the common background image in place of the detected images of the first person to the server preserves the privacy of the detected first person.

20. A system for managing human motion data, comprising:

one or more processors; and
a memory coupled to the one or more processors and storing instructions that, when executed by the one or more processors, cause the system to:
receive a sequence of video images including at least a first person;
for each video image in the sequence of video images,
detect the first person in the video image; and
extract a skeleton figure of the detected first person from the detected image of the first person, wherein the skeleton figure is composed of a set of human keypoints of the detected first person;
combine a sequence of extracted skeleton figures of the detected first person from the sequence of video images to form a first skeleton sequence of the detected first person, wherein the first skeleton sequence depicts a continuous motion of the detected first person; and
transmit the first skeleton sequence of the detected first person along with a common background image associated with the sequence of video images to a server to be stored on the server, wherein the common background image is transmitted only once, wherein transmitting the first skeleton sequence of the detected first person and a single copy of the common background image in place of the detected images of the first person to the server preserves the privacy of the detected first person.

* * * * *